US012223272B2

(12) United States Patent
Mukund et al.

(10) Patent No.: US 12,223,272 B2
(45) Date of Patent: Feb. 11, 2025

(54) SYSTEM FOR NATURAL LANGUAGE PROCESSING OF SAFETY INCIDENT DATA

(71) Applicant: Benchmark Digital Partners LLC, Mason, OH (US)

(72) Inventors: R Mukund, Cincinnati, OH (US); Matthew Bayuk, Austin, TX (US); Natasha Porter, Mason, OH (US); Vijay Alluru, Frisco, TX (US); Charles Malone, Fort Thomas, KY (US)

(73) Assignee: Benchmark Digital Partners LLC, Mason, OH (US)

( * ) Notice: Subject to any disclaimer, the term of this patent is extended or adjusted under 35 U.S.C. 154(b) by 291 days.

(21) Appl. No.: 17/942,853

(22) Filed: Sep. 12, 2022

(65) Prior Publication Data

US 2023/0077338 A1 Mar. 16, 2023

Related U.S. Application Data

(60) Provisional application No. 63/301,553, filed on Jan. 21, 2022, provisional application No. 63/243,231, (Continued)

(51) Int. Cl.
*G06F 3/0481* (2022.01)
*G06F 40/166* (2020.01)
(Continued)

(52) U.S. Cl.
CPC .......... *G06F 40/284* (2020.01); *G06F 3/0481* (2013.01); *G06F 40/166* (2020.01);
(Continued)

(58) Field of Classification Search
CPC .... G06F 3/0481; G06F 40/284; G06F 40/166; G06F 40/242; G08B 21/02
See application file for complete search history.

(56) References Cited

U.S. PATENT DOCUMENTS 10,353,678 B1 * 7/2019 Wagner ............... G06F 11/3604
10,674,965 B2 6/2020 Elhawary et al.
(Continued)

FOREIGN PATENT DOCUMENTS

AU 2017279810 A 2/2023
CN 108961790 A 12/2018
(Continued)

OTHER PUBLICATIONS

Badami, Mahsa, Faezeh Tafazzoli, and Olfa Nasraoui. "A case study for intelligent event recommendation." International Journal of Data Science and Analytics 5 (2018): 249-268. (Year: 2018).*
(Continued)

*Primary Examiner* — Paras D Shah
*Assistant Examiner* — Oluwadamilola M Ogunbiyi
(74) *Attorney, Agent, or Firm* — Dinsmore & Shohl LLP

(57) ABSTRACT

An incident report management system is configured to receive and analyze incident reports relating to workplace accidents and injuries. A natural language processing function utilizes word dictionaries of varying type and scope to reduce an incident description to a set of core components that are far smaller than the input text while also preserving important aspects of the input text. The reduced core component set may be analyzed for meaning, compared to large volumes of historic incident reports, and otherwise processed more quickly and more efficiently whether by an expert function or AI function. In this manner, the system is able to provide real-time feedback during submission of incidents to improve quality and completeness, and after submission of incidents to notify users of serious incidents, provide dashboard analytics, and identify underlying and undiscovered risks in the workplace.

20 Claims, 5 Drawing Sheets

Related U.S. Application Data filed on Sep. 13, 2021, provisional application No. 63/243,190, filed on Sep. 12, 2021.

(51) Int. Cl.
| | |
|---|---|
| *G06F 40/242* | (2020.01) |
| *G06F 40/263* | (2020.01) |
| *G06F 40/284* | (2020.01) |
| *G06F 40/58* | (2020.01) |
| *G08B 21/02* | (2006.01) |

(52) U.S. Cl.
CPC .......... *G06F 40/242* (2020.01); *G06F 40/263* (2020.01); *G06F 40/58* (2020.01); *G08B 21/02* (2013.01)

(56) References Cited

U.S. PATENT DOCUMENTS

| | | | |
|---|---|---|---|
| 10,708,795 B2 | 7/2020 | Tapia | |
| 10,720,050 B2 | 7/2020 | Jeon | |
| 10,733,885 B2 | 8/2020 | Cho et al. | |
| 10,866,848 B2 | 12/2020 | Bridges et al. | |
| 11,748,568 B1* | 9/2023 | Orhan | H04L 43/16 709/224 |
| 11,983,186 B2 | 5/2024 | Acharya et al. | |
| 2013/0111321 A1* | 5/2013 | Dorrell | G06F 40/177 715/215 |
| 2018/0204167 A1* | 7/2018 | Rayner | G06F 3/04817 |
| 2018/0322509 A1* | 11/2018 | Walthers | G06F 40/279 |
| 2019/0007377 A1* | 1/2019 | Bender | H04L 12/1895 |
| 2020/0067985 A1* | 2/2020 | Bhargava | G06F 3/0481 |
| 2020/0302018 A1* | 9/2020 | Turkkan | G06F 40/284 |
| 2020/0372224 A1* | 11/2020 | Azmoon | H04M 3/5133 |
| 2021/0090748 A1 | 3/2021 | Toyoshiba et al. | |
| 2021/0357585 A1* | 11/2021 | Surdeanu | G06F 40/279 |
| 2021/0358584 A1* | 11/2021 | Bastide | G16H 15/00 |
| 2022/0092493 A1 | 3/2022 | Bowers | |
| 2022/0107852 A1* | 4/2022 | Kulkarni | G06F 9/542 |
| 2022/0245539 A1* | 8/2022 | Clearwater | G06Q 10/0635 |
| 2022/0309416 A1* | 9/2022 | Barday | G06Q 10/067 |
| 2024/0118846 A1* | 4/2024 | Kobayakawa | G06F 3/121 |

FOREIGN PATENT DOCUMENTS

| | | |
|---|---|---|
| CN | 109447048 A | 3/2019 |
| CN | 112991743 A | 6/2021 |
| CN | 113178069 A | 7/2021 |
| IN | 202141024097 A | 6/2021 |
| KR | 10-1670412 B1 | 10/2016 |
| KR | 10-2238764 B1 | 4/2021 |

OTHER PUBLICATIONS

Hussain, Faris, et al. "Diagnostic error in the emergency department: learning from national patient safety incident report analysis." BMC emergency medicine 19: 1-9. (Year: 2019).*

Sutejo, Sutejo, Agung Budi Prasetijo, and Farid Agushybana. "Designing integrated patient safety incident reporting with hospital information system." Jurnal Aisyah: Jurnal Ilmu Kesehatan 6.3: 661-666. (Year: 2021).*

* cited by examiner

300

Incident Report

Location: [ Click to Select ]

Date: [ Click to Select ]  ← 302

Time: [ Click to Select ]

Severity: [ Click to Select ]

Description of incident: 304    306

A painter fell from a ladder and was injured.
[+] *The fall was from a height of about* [+] *feet.*
[+] *The painter's* [+] *was injured.*
[+] *The painter fell onto* [+] *.*
[+] *The injury appeared to be* [+] *because the painter was able to* [+] *afterwards.*

| Quality 2/6 | - Text is very short, please elaborate.<br>- Text does not include many descriptive adverbs/adjectives – please add more detail.<br>- Text mentions "fall" but does not include height.<br>- Text mentions "injured" but does not specify a location or extent of injury. |

308    SUBMIT    310

FIG. 6

SYSTEM FOR NATURAL LANGUAGE PROCESSING OF SAFETY INCIDENT DATA

PRIORITY

This application claims the priority of U.S. Provisional Patent 63/243,190, filed Sep. 12, 2021, titled "Potential Serious Injury Artificial Intelligence Advisor," and U.S. Provisional Patent 63/243,231, filed Sep. 13, 2021, titled "Potentially Serious Incident Artificial Intelligence Advisor," and U.S. Provisional Patent 63/301,553, filed Jan. 21, 2022, titled "Executive Artificial Intelligence (AI) Advisor," the entire disclosure of each of which is incorporated by reference herein.

FIELD

The disclosed technology pertains to a system for natural language processing and management of safety incident data.

BACKGROUND

In the health and safety community there is a strong need for understanding both severe injuries and fatalities. Having the ability to accurately classify an event into standard sets of categories allows the community to easily compare events. Accordingly, there is a need for a means to allow the health and safety community to know whether a certain similar event has occurred and know the occurrence rate for that event. Due to the volume of event data, varying sources of event data, and varying formats and approaches to generating event data, there are certain logistical and technical challenges to managing and reacting to such event data. As one example of a logistical problem, manual curation and review of event data is not feasible due to the volume of data and rate of generation, as well as legal and privacy concerns with sharing such data for manual curation. As a result, it is a natural conclusion that some level of automated curation and review may be advantageous.

While there are conventional approaches to managing event data, such as pre-configured rule engines, expert modules, and natural language processing, such conventional approaches face certain technical challenges when implemented for processing safety incident data. For example, conventional approaches to configuring rule engines or expert modules may still require a high level of manual curation initially and overtime, or may require custom implementation of APIs or other interfaces for each data source, or both.

Natural language processing ("NLP") and other artificial intelligence ("AI") approaches are also conventionally limited in their applicability to safety incident data. As one example of a technical challenge of conventional NLP approaches, safety incident data tends to have unique characteristics, structure, and lexicography depending on the industry from which it originates (e.g., a safety incident at an auto assembly plant will be captured and described very differently from a safety incident at a brick and mortar retail location), and so processing by a global or general NLP function will often return inaccurate or unsatisfactory results. As another example, conventional approaches to NLP also benefit from being able to work upon predictable ranges of input, which is difficult or impossible due again to the variety of forms, structures, and sources of safety incident data (e.g., beyond different lexicography, this may also include different data structure and formatting, such as safety incident data from one source being received as a comma separated value string, while data from another source is received as arbitrarily structured XML).

What is needed, therefore, is an improved system for managing and performing NLP for safety incident data.

BRIEF DESCRIPTION OF THE DRAWINGS

The drawings and detailed description that follow are intended to be merely illustrative and are not intended to limit the scope of the invention as contemplated by the inventors.

FIG. 6 is a screenshot of an exemplary guided submission interface usable to receive real-time guidance while submitting an incident dataset.

DETAILED DESCRIPTION

Figure 1:
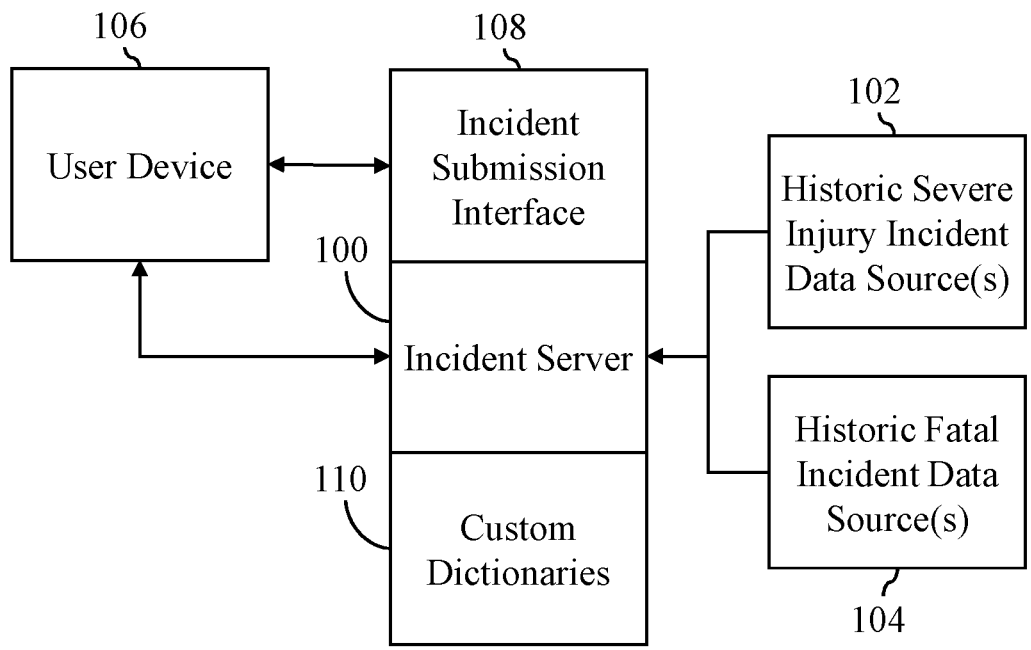
FIG. 1 is a schematic diagram of an exemplary system configured to manage and analyze incident datasets.

The inventors have conceived of novel technology that, for the purpose of illustration, is disclosed herein as applied in the context of natural language processing. While the disclosed applications of the inventors' technology satisfy a long-felt but unmet need in the art of natural language processing, it should be understood that the inventors' technology is not limited to being implemented in the precise manners set forth herein, but could be implemented in other manners without undue experimentation by those of ordinary skill in the art in light of this disclosure. Accordingly, the examples set forth herein should be understood as being illustrative only, and should not be treated as limiting.

Implementations of the disclosed technology address various technical challenges and problems in the application of natural language processing ("NLP") and other analysis of safety incident data and similar datasets. In particular, implementations of the disclosed technology address at least the following: (A) industry-specific filtering capabilities to analysis first reference safety incident datasets and models related to a particular industry before analyzing records against the full knowledge base; (B) due to the complex nature of natural language processing using English as the language being analyzed, a simple statistical model is not able to produce desired outputs to the user; (C) increasing accuracy of analytical results, especially accuracy when determining or identifying 'High-Risk Activity'; (D) increasing completeness of analytical results, as conventional approaches only identify a percentage of critical record; (E) providing output from analytical processing that is more useful, actionable, and apparent; and (F) providing a system and model that is capable of automatically preprocessing safety incident data, in addition to the other features, benefits, and technical challenges described below.

Implementations of the disclosed technology are configured to analyze safety incident datasets resulting from potentially serious incidents ("PSI") and generate insights and a risk profile to show how often similar incidents have previously occurred in industry that have resulted in PSI incidents, such as a severe injury or a fatality. No conventional solutions exist to notify, in near real-time, health and safety personnel and leadership what injuries, fatalities, and related events as they are reported, or during the process of reporting. These real-time alerts may be in the form of texting message, push notification, email, and other electronic alerts to notify the health and safety community of these critical events happening at their worksites, and provide opportunities for pro-active intervention for safety incidents, or in the case of alerts and feedback provided during the process of reporting may be in the form of an interface that provides real-time feedback and guidance as reports are entered (e.g., where a user types "Worker fell from a ladder." the interface may be configured to prompt the user to specify the height of the ladder, the height of the fall, the type of surface below the ladder, and other information).

Turning now to the figures, FIG. 1 is a schematic diagram of an exemplary system configured to manage and analyze incident datasets. An incident server (100) is configured to provide an incident submission interface (108), receive and analyze incident datasets submitted via the incident submission interface (108), maintain and utilize one or more custom dictionaries (110) during analysis of incident datasets, and receive historic, prior, or previous incident datasets from one or more historic incident databases (102, 104) that are utilized to build analytical models and in analyzing current incident datasets. The incident server (100) may include one or more physical, virtual, cloud, or other servers or computing environments, with each server comprising one or more processors, memories, communication devices, user interface devices, and other components as may be useful in receiving, transmitting, storing, modifying, analyzing, and otherwise processing data. When described herein, other computing devices should be understood to include some or all of the preceding components described in the context of servers.

The incident submission interface (108) may be provided or exposed by the incident server (100), and may be variously implemented as a graphical user interface or communication interface via a website, web service, web portal, application programming interface ("API"), native software application, mobile device application, or other communication channel or interface. A user device (106) (e.g., a smartphone, computer, or other computing device) may be in communication with the incident server (100) via the incident submission interface (108), and may also be in communication with the incident server (100) to receive analytics and information related to incident dataset analysis via a dashboard interface, or via electronic communication such as text messaging, email, application notifications, automated telephone calls, and other electronic communications.

The custom dictionaries (110) maintained by the incident server (100) may include a plurality of dictionaries each including one or many words or phrases, and with each dictionary being associated with a particular step of incident dataset analysis, and also associated with a particular scope of incident dataset analysis. It should be understood that when used herein, descriptions of a "word" or "words" should be understood to include both singular words (e.g., "walked", "lost"), as well as phrases combining several individual words (e.g., "walked under", "walked over", "lost consciousness") unless the context of such use is expressly or implicitly confined to an individual word. While the content and use of dictionaries (110) will be described in more detail below, dictionary types may include an imprecise word dictionary (e.g., words that may have different meanings in different contexts, such as "under fire", "lead", or "fine"), a stop word dictionary (e.g., words that have little value in natural language processing, such as "can", "cannot", "cant", "can't", "he", "he'd", "he'll", and so on), and a risk word dictionary (e.g., words that have high value in natural language processing for identifying and determining safety risks, such as "cutting", "climbing ladder", "hand slipped", or "sawblade").

In addition to defining words, dictionaries may also define spatial and sequential associations between words such as may be configured by a regular expression or other logic. As an example, a risk word dictionary might define a risk word as "hit" when used proximately to "face", "body", or "limb" (e.g., where proximity is expressed as a number of separating characters or individual words, such as "hit" within five words of "face"), or might define a risk word as "hit" when used in a sentence before "face", "body", or "limb" (e.g., regardless of proximity, "hit" must sequentially precede "face").

Dictionaries may also be associated with varying scopes of application. As an example, dictionary scopes may include a global dictionary (e.g., applicable to all incident datasets), a field specific dictionary (e.g., applicable to incident datasets arising from a particular field or industry, such as "manufacturing", "retail", or "construction"), an organization specific dictionary (e.g., applicable to a particular organizational instance of the system, such as incident datasets arising from an organizational user "Sample Organization, Inc."), a location specific dictionary (e.g., applicable to incident datasets arising from particular geographical locations, such as hot/cold climate dictionaries, state specific dictionaries, an indoor incident dictionary, an outdoor incident dictionary, and so on), and other dictionary scopes. As will be apparent, the number, type, and purpose of dictionaries will vary by implementation, and may also vary by organization or end user. For example, one implementation may utilize global dictionaries for stop words, imprecise words, and risk words, as well as field specific dictionaries for stop words, imprecise words, and risk words.

Dictionaries may also include additional attributes, characteristics, and other metadata associated with words. As one example, this may include mappings or associations between similar words and/or to categorical words, such as an association within a risk word dictionary of a plurality of similar terms (e.g., "hit", "strike", "knock", "slam", "collide") to a representative categorical word (e.g., "physical strike")

As illustrated by FIG. 1, the databases (102, 104) may include one or several sources of historic incident data, such as one or several sources of historic severe injury incident datasets (102) and one or several sources of historic fatal incident datasets (104). The databases (102, 104) may be publicly available data sources, private data sources, or both, and records may be received from the databases (102, 104) as needed, or may be received from the databases (102, 104) and stored in a local database based upon scheduled data retrievals or synchronizations to ensure that the incident server (100) maintains a complete dataset for analysis.

Figure 2:
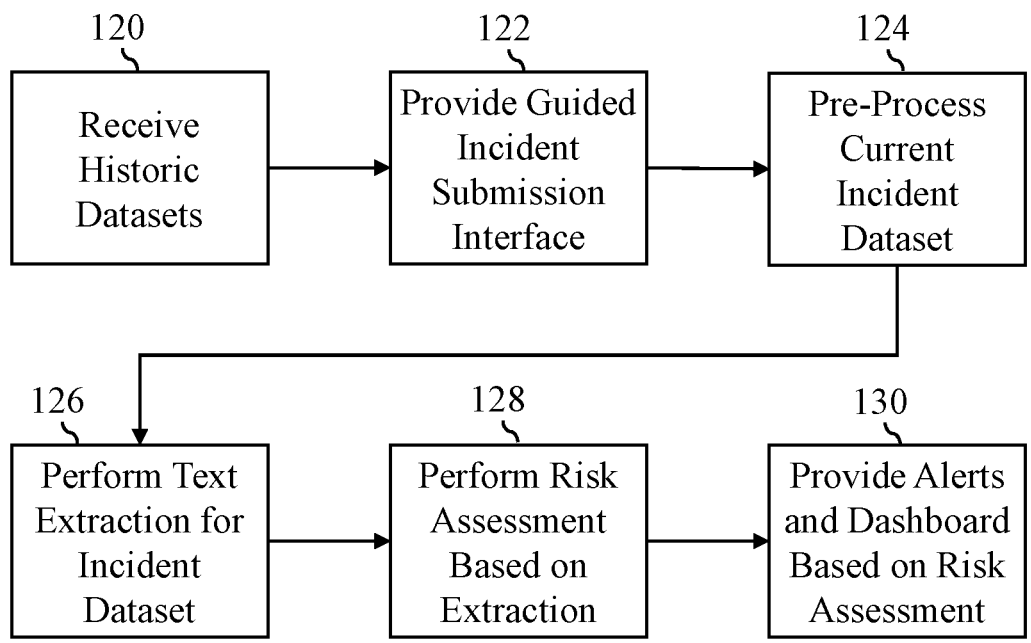
FIG. 2 is a flowchart of an exemplary set of high-level steps that could be performed by a system to manage and analyze incident datasets.

Turning now to FIG. 2, that figure shows a flowchart of a set of high-level steps that could be performed by a system, such as that illustrated in FIG. 1, to manage and analyze incident datasets. The system may be configured to receive (120) historic incident datasets from one or several sources (102, 104), and may store those received (120) datasets for use in analysis of current incident datasets, which in varying implementations may include search and comparison of historic incidents, production of analytical models or other functions based on historic incidents, or both. As has been described, historic incident datasets may be received (120) in response to queries as needed, or may be received (120) based upon scheduled or intermittent synchronization to capture new records, for example.

The system may also provide (122) a guided incident submission interface (108) that is configured to allow a user to submit an incident dataset, and to provide real-time feedback to the user during submission of the incident dataset. The system may also pre-process (124) a current incident dataset, such as may be received via the submission interface (108). Pre-processing (124) will be described in more detail below, but for example may include preparing and optimizing text descriptions of the incident in order to improve the speed and accuracy of subsequent processing of the text descriptions by other analytical functions. The system may also perform (126) text extraction on the incident dataset in order to identify and classify risk words in the text descriptions, and produce core components of the incident from the incident description.

The system may also perform (128) one or several risk assessments based on the incident dataset, which may include providing information and context for comparable incidents contained in the historic incident datasets, and may include identifying undiscovered underlying risk factors that may contribute to future incidents. Based on the preceding analysis and comparison of the current incident dataset and prior incident datasets, the system may also provide (130) incident alerts (e.g., text messages, automated phone calls, emails, and other electronic communications) to one or several recipients that are configured and associated with the incident, and may also provide an incident dashboard as a graphical user interface displaying information such as descriptions of past and prior incidents, descriptions of comparable incidents identified in the historic incident datasets, descriptions of undiscovered underlying risk factors identified (128) by a risk assessment, and other information.

The quality of the incoming severe injury and fatality descriptions submitted as part of incident datasets have a strong effect on the accuracy and quality of subsequent analysis performed by the system. Because of this strong correlation, it is advantageous for an incident management system to perform real-time analysis of the incoming event descriptions so that they may be corrected or updated by the submitting user prior to submission, or immediately after submission. In some implementations, this may include providing feedback on the incident dataset while the user is composing the event description so that the user can see when their event description is low quality or missing key information and make any corrections.

Figure 3:
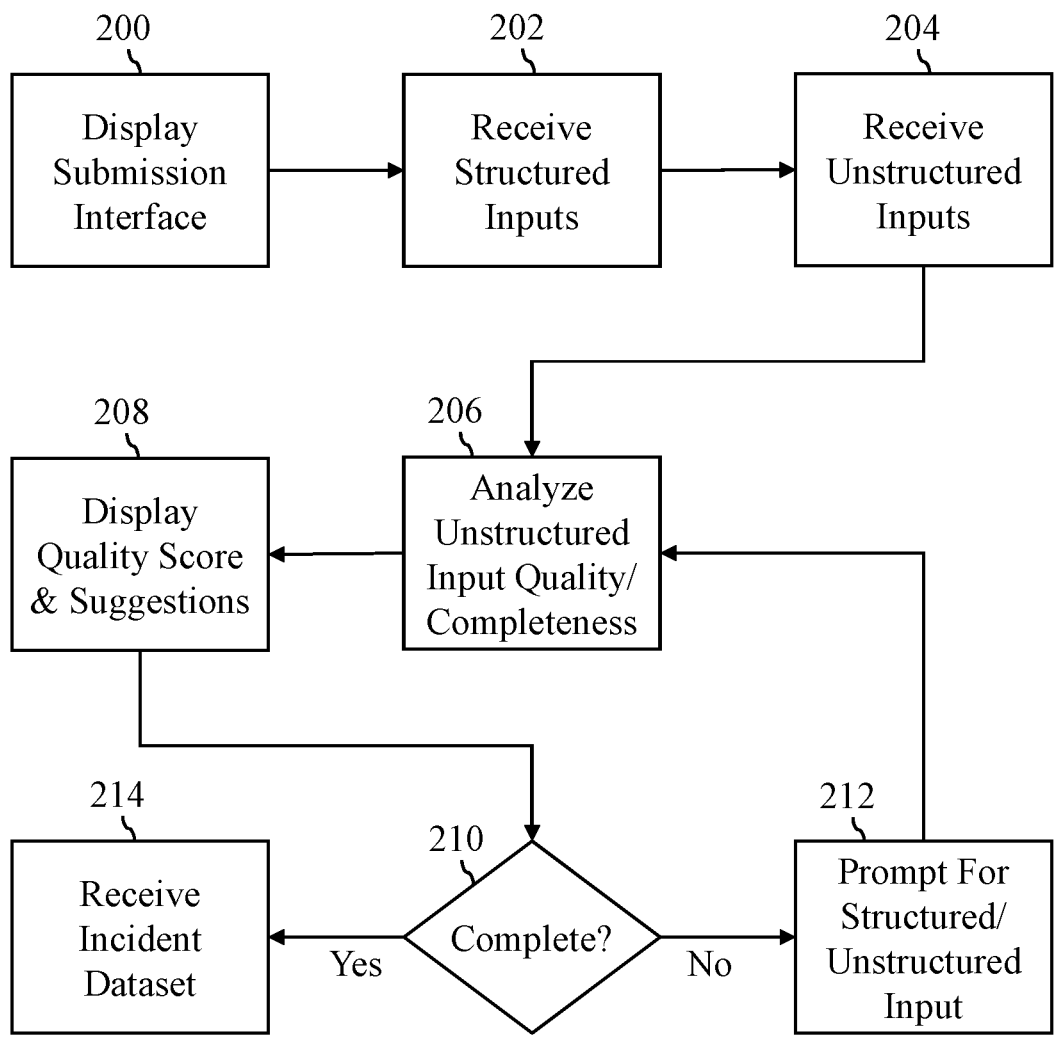
FIG. 3 is a flowchart of an exemplary set of steps that a system could perform to provide an incident submission interface.

As an example of the above, FIG. 3 is a flowchart of a set of steps that a system could perform to provide an incident submission interface as has been described above in the context of FIGS. 1 and 2, while FIG. 6 provides an illustrative example of a submission interface (300) that may be displayed on a user device. With reference first to FIG. 3, the system may cause a submission interface to be presented (200) on a display of user device, which may include providing the graphical user interface via a browser directed to website or other web based application, via a native software application configured on the user device, or via another interface (108) as has been described above. As the user provides inputs and makes selections as prompted by the presented (200) interface, the system may receive (202) structured inputs (e.g., menu selections, radio button selections, or selections of other pre-configured inputs), and may receive (204) unstructured inputs (e.g., free-form text descriptions and text strings).

In some implementations, these inputs may be received (202, 204) by the system in real-time as they are entered into the form by the user, and prior to submission of the form (e.g., prior to the user clicking a submit button as illustrated in FIG. 6), while in other implementations these inputs may be received (202, 204) by the system after the form is completed and submitted by the user (e.g., by clicking a submit button as illustrated in FIG. 6). In implementations where inputs are received (202, 204) prior to submission, this may include configuring the presented (200) interface to utilize client side scripts or other functions that transmit inputs in real time (e.g., asynchronous communication to the server) as they are entered on the client device, or may include configuring a native software application installed on the client device to perform a similar function, for example.

The system may then analyze (206) the received (202, 204) inputs for quality and completeness using one or more of a pre-configured expert function, NLP function, other artificial intelligence function, or other analytical function. Analysis (206) of the unstructured input may be based entirely on the content of the unstructured input, but may also be based in part upon structured inputs (e.g., where a structured input indicates that the incident included a serious injury or fatality, analysis of the unstructured input for quality and completeness may be more stringent as compared to a structured input indicating only a minor or superficial injury).

Factors considered by the analytical function (e.g., expert function, NLP function, AI function) will vary based on the one or more types of functions used during analysis (206) in a particular implementation. With respect to quality, factors may include for example overall length of the incident description, number of meaningful words in the incident description (e.g., after removing imprecise words and/or stop words based upon one or more dictionaries, as will be described in more detail below), number of risk words in the incident description (e.g., identified based upon one or more risk word dictionaries, as will be described in more detail below), descriptiveness (e.g., based upon the frequency of adjectives, adverbs, and other modifiers included in the description), similarity to historic incident descriptions (e.g., based upon a fuzzy logic search and comparison of historic incident datasets), similarity to other high quality descriptions (e.g., based upon an AI function analysis of the incident description, where the AI function has been configured or trained based upon manually curated and annotated datasets that exhibit positive and negative aspects of high quality descriptions), and other factors.

With respect to analysis (206) for completeness, relevant factors may include for example presence of important information corresponding to part of a structured input (e.g., where a structured input indicates a serious or fatal injury, but the text description does not include a description of the injury), presence of important information based upon other portions of the text description (e.g., where the unstructured input describes an injury related to a "fall" or a "ladder", but does not specify the height from which the fall occurred), and other factors. As further explanation of the preceding scenario, where the analysis (206) identifies an incomplete incident component in the unstructured input (e.g., "fall"), the system continues to search the unstructured input for a component descriptor (e.g., "height of 8 feet") that may be combined with the incomplete incident component to provide a complete incident component (e.g., "fall height of 8 feet").

Based upon an analysis (206), the system may then determine and display (208) a quality score or other indication of incident description quality via the presented (200) interface, may display one or more suggestions related to the description's quality or completeness, or both. As an example, a displayed (208) quality score may be a scaled numerical description (e.g., between 1 and 100, between 1 and 6, etc.) that is based upon analysis (206) of the unstructured input's quality. As further example, this may include analysis (206) by an expert module pre-configured with a rule set to determine whether the incident description falls within one of several ranges based on the number of meaningful words, and to determine whether the descriptiveness falls within one of several ranges based on the frequency of noun modifiers, where the quality score is a factor of the ranges that the description falls within for each factor.

When displaying (208) suggestions related to description quality, the system may provide pre-configured feedback based on the quality determination. Continuing the prior example, where the system determines that the description includes 30 meaningful words and falls within a "moderate quality" range for length, and also includes 10 noun modifiers and falls within a "moderate quality" range for descriptiveness, the system may display (208) suggestions such as "Your description is too short, please add 2-3 more sentences," or "Your description isn't very detailed, please add adjectives and adverbs to modify the nouns."

When displaying (208) suggestions related to description completeness, the system may provide pre-configured similar to the above, or may provide semi-dynamic feedback based on particular aspects of completeness. Continuing the prior example, where the system identifies "fall" or "ladder" as meaningful words or risk words within the text description, but is unable to identify a description of the height of the fall, or a description of whether any safety equipment was in use to mitigate the risk of injury, the system may display (208) suggestions such as "Your description mentions a fall, please describe the height of the fall," or "Your description mentions a fall, please describe whether any safety equipment was in use at the time of the fall."

In some implementations, the system may be configured to prevent submission of the incident dataset until requirements for quality and or completion (210) are met. Continuing the above example, the system may prevent submission of the incident dataset until the text description is revised to indicate the height from which the fall occurred. Where the system determines that a description is not complete (210), the system may prompt (212) the user for additional structured and/or unstructured inputs by providing suggestions, as described above, and/or additional structured input elements, such as by causing the presented (200) interface to display a new structured input element that the user may interact with to specify the height of the fall.

Where the system determines that the unstructured input meets any requirements for quality or completeness (210), or where the system allows a user to submit an incident dataset without meeting requirements, the user may click a submit button or otherwise complete the submission to cause the system to receive (214) the incident dataset.

With reference to FIG. 6, the interface (300) includes a first section (302) that is configured to receive structured inputs from the user (e.g., such as a selection of a location of the incident from a drop-down list pre-populated with work locations for that particular organization or end user, or a selection of a radio button, checkbox, or other input element). A second section (304) is configured to receive unstructured inputs, such as free-form text, so that the user may provide a description of the incident. An initial incident description provided by a user in the second section (304) is displayed in standard format text and indicates that "A painter fell from a ladder and was injured."

A quality indicator (308) displays a quality assessment for the provided text description on a numerical scale of 1 to 6 (e.g., though it should be understood that a variety of numerical, text, or visual scales are also possible, just as a green/yellow/red visual indicator), with a 6 being the highest quality post based on analysis (206) of the unstructured content as described above. A suggestion pane (310) provides a number of suggestions related to the quality and completeness of the incident description and is also based on analysis (206) of the unstructured content as described above. Related to the suggestion pane (310), the second section (304) also includes a set of four suggested changes (306) that may be made to the incident description displayed in an italics format, and are determined and provided based upon the analyses (206) of the unstructured content in order to improve the quality and/or completeness of the description.

As an example with reference to the first suggested change (306), a user may select the first "+" button to add the text "The fall was from a height of about _____ feet" to the incident description, and may select the second "+" button to populate an integer for a number of feet of the fall (e.g., either by typing in the number of feet, or selecting the number of feet from a pre-populated selection menu or other structured input element). In some implementations, the system may also provide a suggested value for any variable data in the suggested change (306) based upon a pre-configured value or averages from historic incident datasets (e.g., where analysis of historic ladder falls indicates an average fall height of about 6 feet, the system may pre-populate that input element with a selection corresponding to 6 feet). As should be apparent in light of this disclosure, the features, functions and components of the submission interface (300) shown in FIG. 6 are exemplary, and varying implementations of the system may include additional features, exclude shown features, or arrange components of the interface (300) differently.

Figure 4:
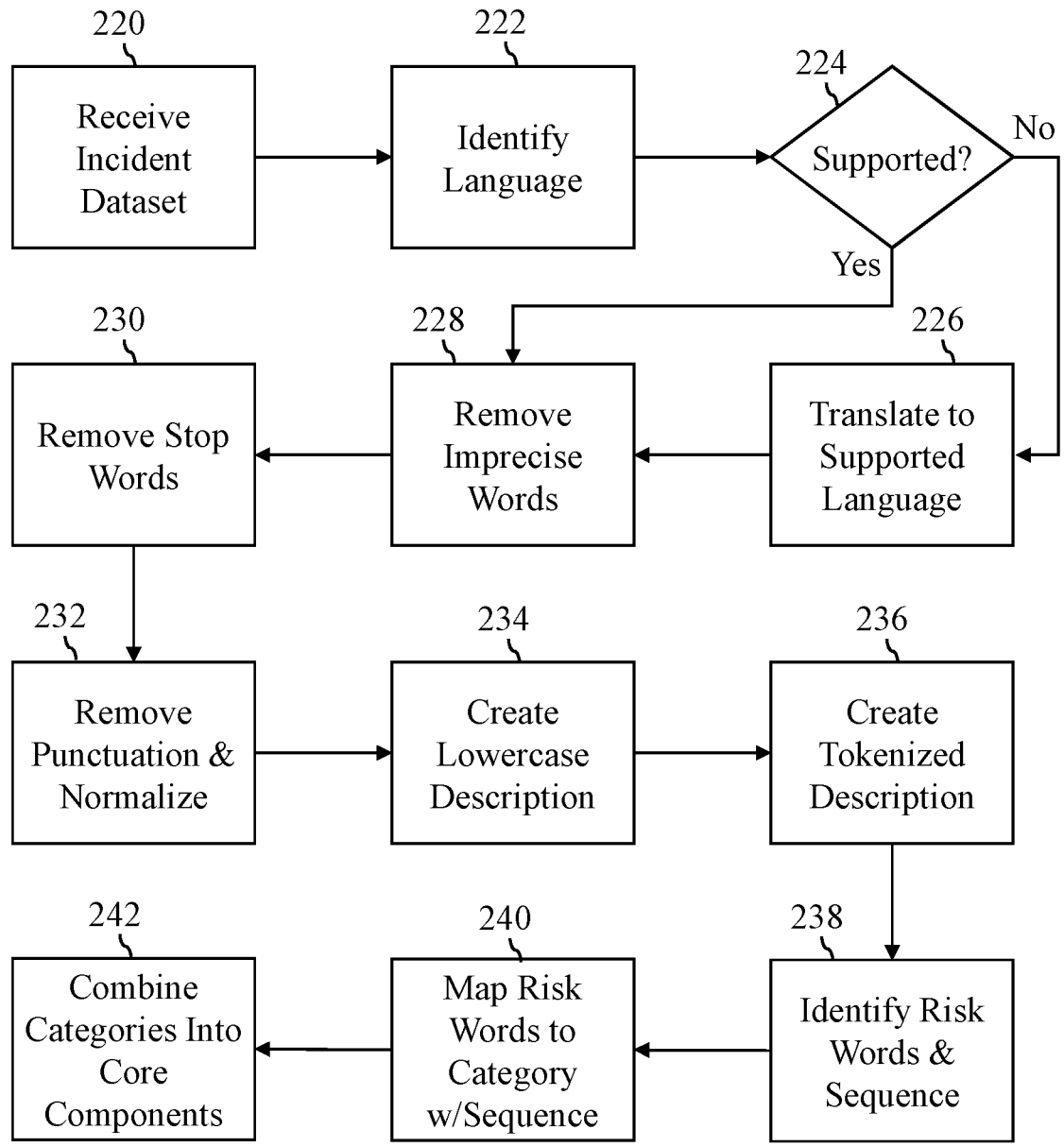
FIG. 4 is a flowchart of an exemplary set of steps that a system could perform to preprocess an incident dataset.

Turning now to FIG. 4, that figure is a flowchart of a set of steps that a system could perform to preprocess an incident dataset and extract core components of the incident description, as has been described in the context of the steps (124, 126) of FIG. 2. Upon receiving (220) an incident dataset (e.g., after submission via a submission interface (108)), or alternately upon receiving partial inputs (202, 204) related to an incident submission that is still in progress, the system may identify (222) a language of the text description of the incident included in the dataset using an expert function, NLP function, or other function. Where the language (222) is not supported (224) by the system, the system may translate (226) the description to a supported language using a language translation function. Languages supported (224) by the system will typically depend upon the languages that custom dictionaries (110) are configured to support, as well as the capabilities of the NLP function or expert function used to analyze the text description, but it would not be uncommon for a particular implementation to only support a single language.

In some implementations, the translation function (226) may be a standard translation function that is configured or modified based upon one or more of the custom dictionaries (110) maintained by the system and applicable to the incident dataset in order to give preference to meaningful words and risk words defined in the dictionary during translation. For example, where a categorical risk word "physical strike" is defined and associated with a number of variable words describing physical strikes, the translation function (226) may be configured to translate all of those variable words to "physical strike" instead of translating to an intermediate word. As another example, where a stop word "accordingly" is defined, the translation function (226) may be configured to filter that stop word at the time of translation instead of translating into an intermediate word that is later filtered out based upon the stop word dictionary.

After translation (226), or where the identified (222) language is supported (224), the system may filter the incident description to remove (228) any imprecise words based on one or more imprecise word dictionaries, and remove (230) any stop words based on one or more stop word dictionaries. This may include filtering words (228, 230) based on global or default dictionaries defining stop words and imprecise words, and may also include removing stop words and imprecise words based on one or more custom dictionaries applicable to the incident dataset (e.g., such as a field or industry specific, organization specific, location specific, or other custom dictionary). The system may also filter the incident description to remove (232) punctuation, and may also filter the incident descriptions to remove or replace integers and other non-text symbols with text equivalents (e.g., replacing the integer "8" with the word "eight").

As a further step of NLP pre-processing for subsequent analysis, the system may create several variations of the current incident description (e.g., as may have been modified in relation to translation (226) and filtering (228, 230, 232) or the original unmodified incident description (e.g., creation of variations may occur prior to some or all of the filtering (228, 230, 232) steps). This may include preserving the current modified description, creating (234) a second description based upon a lowercase conversion of the modified description, and creating (236) a tokenized description based upon the modified description. The preserved description is not changed during this stage of pre-processing, and is useful input to an NLP or other analytic function since the meaning of certain words and phrases may change when using different forms of capitalization (e.g., such as "Buffalo," in reference to Buffalo, NY, and "buffalo," in reference to an animal).

The lowercase conversion description is useful as input to an NLP or other analytic function since all of the words have been normalized to lowercase form, which allows for faster and more efficient analysis during subsequent processing by a NLP function or other function. The tokenized description is useful as input to an NLP or other analytic function because it allows for additional and more advanced forms of processing by an NLP function. For example, a tokenized form allows for text parsing and tagging, which is advantageous or required by some NLP functions.

The system may then identify (238) any risk words contained in the incident description (e.g., analyzing one or all of the preserved description, lowercase conversion, and tokenized description) based upon one or more risk word dictionaries, which may include a global risk word dictionary, as well as an industry or field specific, organization specific, location specific, or other custom dictionary, while also preserving the sequence and/or spatial relationship of risk words, as has been described. In some implementations, the order of varying steps illustrated in FIG. 4 may be in a different sequence and/or in parallel, depending upon the number and type of dictionaries (110) applicable to a particular incident dataset. For example, global or general purpose dictionaries that have a very large scope of applicability will typically be less accurate or relevant than custom dictionaries with a narrower scope of applicability, and in general the narrower a scope of applicability is for a particular dictionary the more accurate and relevant the dictionary is for the incident dataset.

As further explanation, a global risk word dictionary (e.g., broad scope of applicability) may define the word "railcar" as a risk word, while an organization specific stop word dictionary (e.g., narrow scope) may define the word "railcar" as a stop word. In such a scenario, the system may apply the dictionaries for their respective purposes starting with the narrowest dictionaries and moving outwards to the broadest dictionaries, such that "railcar" will be filtered out as a stop word rather than being flagged as a high relevance risk word.

After identifying (238) risk words, the system may map (240) the risk words to a subset of categorical risk words or risk types (e.g., as described above in the context of associating "hit", "strike", and "collide" with a categorical risk word or type of "physical strike"), while still preserving the sequence and/or spatial relationship, as has been described. Mapping (240) risk words to categories in this manner advantageously reduces the number of discrete risk words that must be processed by subsequent analytical functions, and allows those functions to provide results more quickly and more efficiently. As an example, a global risk word dictionary in a particular implementation might include about 650 distinct risk words, and may map (240) those distinct risk words to a subset of about 300 distinct categorical risk words or types. The system may then combine (242) the incident description categorical risk words to create one or several core components of the incident description. A core component of the incident description refers to one or several sub-portions of the incident description that have been pre-processed and remapped (240) as described above, and represent a greatly simplified and minimized version of the incident description, while still being highly descriptive of the incident.

By performing pre-processing and NLP functions as described, unpredictable and highly variable incident descriptions can be reduced down to a standardized and consistently classified set of core components that are still representative of the original meaning of the descriptions. Reduced to a set of core components, the incident description is optimized for further processing by NLP functions, AI functions, and other functions. As an example with reference to FIGS. 3 and 6, supposing that the original description entered by the user in the second section (304) was much longer (e.g., several paragraphs), it would not be feasible for a system to receive (204) and analyze (206) unstructured inputs in order to provide real time feedback to the user while they are still in the process of completing the submission.

By reducing the several paragraph long description to a minimized set of core components, the system is able to rapidly analyze (206) those core components using additional NLP functions, or a machine learning or other AI function to identify patterns within core components, or similarities to incidents in historic incident datasets, which enables the system to rapidly provide feedback and suggestions, as has been described. Processing of the original text in a similar manner would take far longer, and would likely result in the user submitting and completing their report long before any feedback or suggestions were provided, resulting in lower quality incident reports over time. Additionally, processing of the original text requires substantially more resources, and more advanced resources as compared to processing of the reduced core components.

For example, complex machine learning, neural network, and other AI functions that are capable of processing large amounts of data require graphical processing units (GPUs) in order to provide results within a reasonable timeframe, whereas processing by NLP or AI functions of the core components can be performed on simpler and cheaper central processing units (CPUs). Because of the high dimensional level of linear algebra required when processing ordinary text descriptions with complex AI functions, a GPU is required to speed up the rate the output is generated so that it is available while still relevant and/or actionable, since a standard CPU would take a considerably longer amount of time to provide output.

Additionally, relying upon complex AI functions to analyze and compare free form text such as incident descriptions is also problematic because such approaches and models tend to 'over-fit' to their data. 'Over-fitting' is a data science term that describes a model that is too tightly correlated to the source data. This 'over-fitting' causes incorrect classifications and other related problems when scaling. As has been described, implementations using the unconventional approaches and processes described above (e.g., conventionally accepted approaches to similar NLP processing include Convolutional Neural Networks using PyTorch, TensorFlow, or an equivalent) greatly improves the speed at which output becomes available, reduces the resources required to provide output (e.g., CPUs may be utilized instead of GPUs while still providing relevant output), and avoids concerns related to 'over-fitting.'

Figure 5:
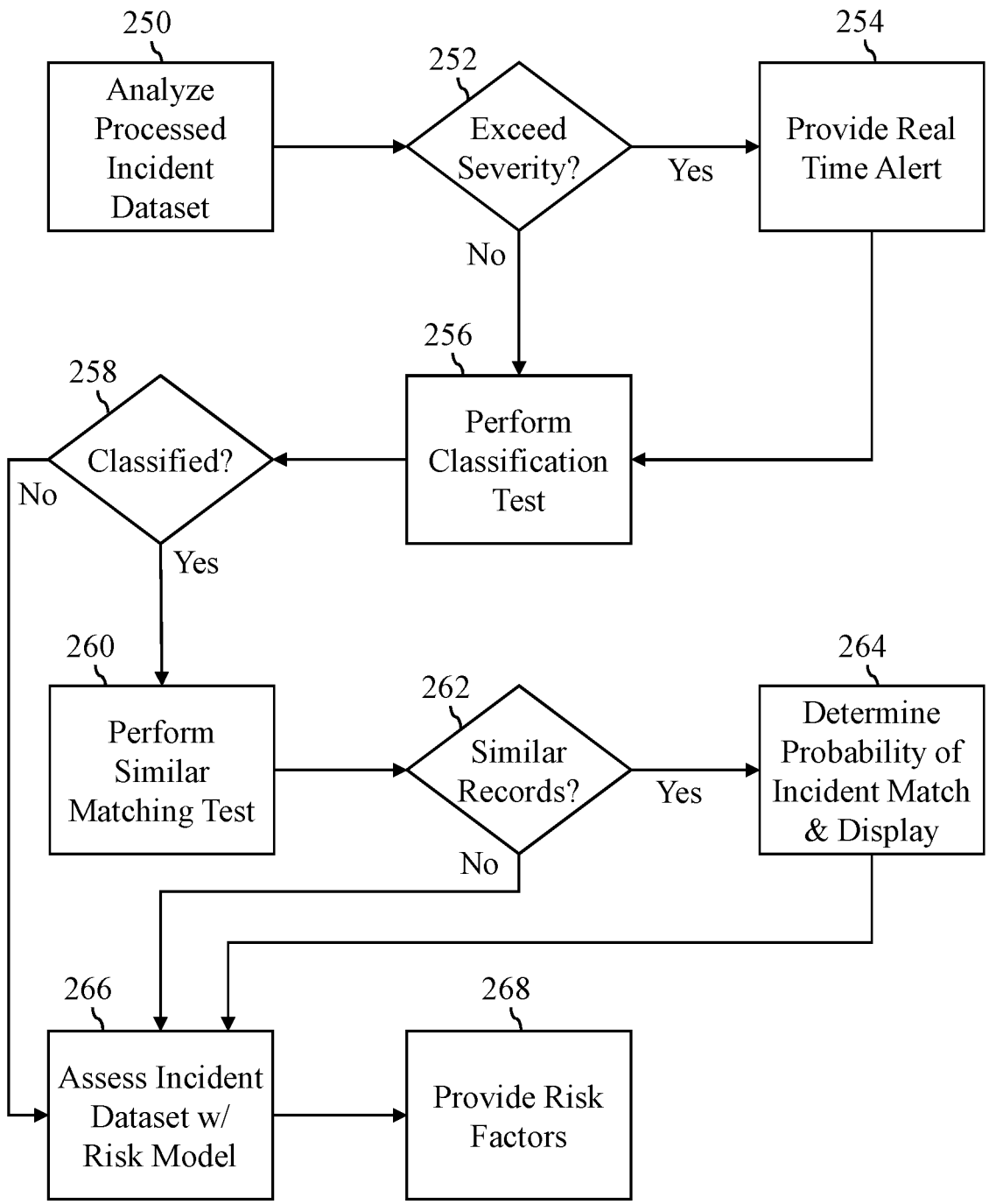
FIG. 5 is a flowchart of an exemplary set of steps that a system could perform to provide real-time incident alerts and incident risk assessments.

Turning now to FIG. 5, that figure shows a flowchart of a set of steps that a system could perform to provide real-time incident alerts and incident risk assessments. When a pre-processed and minimized incident dataset becomes available (e.g., such as upon completion of steps such as those of FIG. 4), the system may analyze (250) the processed incident dataset to determine if a configured severity threshold has been exceeded (252). This analysis (250) may be performed by a NLP function, expert function, or other analytic process configured to determine severity based upon core components and other information of the processed incident dataset.

Where a the severity threshold is exceeded (252), the system may provide real time alerts to one or more recipients, which may include electronic communications such as text messages, emails, application notifications, automated phone calls, or other alerts. Whether or not the threshold is exceeded (252), the system may perform further analysis to determine if the incident qualifies as a PSI. Such analysis may include performing (256) a classification test on the core components identified in the processed incident dataset, which may include searching the historic incident datasets (102, 104) for incidents with similar classifications and core components as those of the current processed incident dataset. If a matching or similar classification is not found (258), the system may report that there are no similar injuries or fatalities within the database.

Where a classification (258) is found, the system may then perform (260) a similar matching test, which may include using a fuzzy logic framework to determine the number of possibly similar injuries or fatalities that exist in the historic event dataset (102, 104). If the number of matches is zero, then the similar matching test is not met (262), and the model will indicate that there are no similar injuries or fatalities within the database.

In some implementations, the model is configured to utilize a fuzzy logic leviathan distance matching measurement, meaning that rather than assessing if something is or is not in the database, it provides varying degrees of truth and determines how strings of text compare to one another. This comparison may be calculated by an index score from 0 to 100, with a higher number indicating a better match. Once this fuzzy logic string match is calculated, a probability density function is conducted for a normal distribution to determine (264) the frequency or likelihood that a similar injury incident or fatality incident exists in one or more of the historic incident datasets (102, 104). This probability may be expressed a score or confidence rating between 0 and 1 (e.g., or an alternative scale) that illustrated the likelihood that a similar injury, fatality, or other incident exists in the historic incident datasets (102, 104).

After identification and/or classification of the incident as a PSI, whether or not successful, the system may also assess (266) the incident dataset using a risk assessment function, which may be implemented as one or more of an expert function, machine learning model or other AI function, or NLP function, for example. Since the pre-processing and subsequent processing of the incident dataset produces consistent classifications, the system may further utilize the incident dataset to forecast metrics related to these standard classifications. In some implementations, this forecasting AI solution may use a Monte Carlo and/or Markov Chain simulation framework, and may also utilize a machine learning adjustment layer that adapts the simulations results in real-time using recent incident data.

After assessing (266) the incident dataset, the system may provide (268) one more identified risk factors via alerts (254), or via a graphical user interface or dashboard as has been described above. Identified risk factors will often include undiscovered underlying risk factors, such as a series of injury incidents being related to each other by non-obvious factors such as time of day, weather, or the location in which they occur. For example, a ladder fall injury, slip and fall injury, and heavy equipment injury might appear unrelated at a high level since the cause of injury in each case seems to be self-evident. However, a deeper assessment (266) of risk factors may identify that all of the incidents occurred in the same room or location within a facility, and so the true risk factor giving rise to incidents may be the layout or dimensions of that room.

Unless the context clearly requires otherwise, throughout the description and the claims, the words "comprise," "comprising," and the like are to be construed in an inclusive sense as opposed to an exclusive or exhaustive sense; that is to say, in the sense of "including, but not limited to." Words using the singular or plural number also include the plural and singular number, respectively. Additionally, the words "herein," "above," and "below" and words of similar import, when used in this application, shall refer to this application as a whole and not to any particular portions of the application.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art.

For instance, the examples, embodiments, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

The invention claimed is:

1. A system comprising:
   (a) an incident server comprising one or more processors;
   (b) a set of dictionaries, wherein each dictionary of the set of dictionaries defines a plurality of words and is associated with a dictionary type and a dictionary scope; and
   (c) a set of prior incident data, wherein the set of prior incident data comprises a plurality of
   prior incident datasets that each describe a past incident;
   wherein the one or more processors are configured to:
      (i) cause an incident submission interface to display on a display of a user device, and receive a set of partial inputs via the incident submission interface, wherein the set of partial inputs comprises a provisional incident description that is received as unstructured data;
      (ii) analyze the provisional incident description to determine a quality score that indicates a level of descriptiveness and, in response to determining that the quality score is less than a maximal quality score, display one or more suggested changes via the incident submission interface, wherein the incident submission interface displays one or more user input controls to be selected by a user in response to the one or more suggested changes;
      (iii) in response to determining that the one or more suggested changes are displayed, receiving a user selection, via the one or more user controls, to cause the incident submission interface to revise the provisional incident description and receive an incident dataset that includes an incident description as unstructured data via the incident submission interface, and pre-process the incident description using a preprocessing function and based on the set of dictionaries;
      (iv) using a core component function and based on the set of dictionaries, identify a plurality of risk words in the incident description and map each of the plurality of risk words to one of a plurality of categorical risks to produce a set of core components;
      (v) using a natural language processing ("NLP") function, compare the set of core components to the set of prior incident data to identify one or more prior incident datasets that are similar to the incident dataset; and
      (vi) provide an incident alert to one or more user devices based on the one or more identified prior incident datasets.

2. The system of claim 1, wherein the one or more processors are further configured to:
   (i) identify an incomplete incident component in the provisional incident description;
   (ii) determine whether a component descriptor that corresponds to the incomplete incident component is contained in the provisional incident description; and
   (iii) where the component descriptor is not contained in the provisional incident description, display a suggested changes via the incident submission interface that describes the incomplete incident component and an expected component descriptor.

3. The system of claim 2, wherein the set of partial inputs includes at least one structured data input, and wherein the one or more processors are further configured to identify the incomplete incident component based on the at least one structured data input.

4. The system of claim 1, wherein the one or more processors are further configured to, when using the pre-processing function to pre-process the incident description:
   (i) identify a language of the incident description;
   (ii) where the language is not a supported language, translate the incident description to the supported language; and
   (iii) remove punctuation from the incident description.

5. The system of claim 1, wherein the one or more processors are further configured to, when using the pre-processing function to pre-process the incident description:
   (i) remove a set of stop words from the incident description based on one or more stop word dictionaries of the set of dictionaries; and
   (ii) remove a set of imprecise words from the incident description based on one or more imprecise word dictionaries of the set of dictionaries.

6. The system of claim 5, wherein the one or more stop word dictionaries comprise a global stop word dictionary and an industry specific stop word dictionary.

7. The system of claim 1, wherein the one or more processors are further configured to, when using the pre-processing function to pre-process the incident description:
   (i) create a lowercase conversion description based on the incident description; and
   (ii) create a tokenized description based on the incident description.

8. The system of claim 1, wherein the one or more processors are further configured to, when using the core component function:
   (i) identify the plurality of risk words in the incident description based on one or more risk word dictionaries of the set of dictionaries;
   (ii) for each risk word of the plurality of risk words, identify a corresponding categorical risk of the plurality of categorical risks; and
   (iii) replace each risk word in the incident description with the corresponding categorical risk for that risk word to produce the set of core components.

9. The system of claim 8, wherein a total number of risk words defined in the one or more risk word dictionaries is greater than a total number of the plurality of categorical risks.

10. The system of claim 8, wherein the one or more risk word dictionaries comprises a global risk word dictionary and an industry specific risk word dictionary.

11. The system of claim 8, wherein the one or more risk word dictionaries define at least one risk word based upon the presence of a first discrete word in a text and the first discrete word's sequence relative to a second discrete word in the text.

12. The system of claim 1, wherein the one or more processors are further configured to, when using the NLP function:
   (i) perform a classification test by comparing the set of core components to the set of prior incident data to identify at least one prior incident dataset having core components that match at least some of the set of core components of the incident dataset;

(ii) perform a similar matching test by comparing the set of core components to the set of prior incident data to identify one or more prior incident datasets that are similar to the incident dataset; and
(iii) determine a probability that a similar prior incident dataset is contained in the prior incident dataset.

13. The system of claim 12, wherein the one or more processors are further configured to:
(i) when performing the similar matching test, compare the set of core components to the set of prior incident data using a fuzzy logic framework; and
(iii) determine the probability that a similar prior incident dataset is contained in the prior incident dataset using a probability density function for a normal distribution.

14. The system of claim 1, wherein the one or more processors includes at least one central processing unit ("CPU"), and does not include any graphical processing unit ("GPU").

15. The system of claim 1, wherein the one or more processors are further configured to:
(i) receive a first result set from a severe injury incident data source, wherein the first result set comprises a first set of incident datasets associated with severe injuries;
(ii) receive a second result set from a fatal incident data source, wherein the second result set comprises a second set of incident datasets associated with fatal incidents; and
(iii) add the first result set and the second result set to the set of prior incident data.

16. The system of claim 1, wherein the one or more processors are further configured to, when displaying the one or more suggested changes via the incident submission interface, display the one or more user input controls that are configured to revise the provisional incident description based upon a corresponding suggested change when selected by the user.

17. A method comprising, by one or more processors of an incident server:
(a) causing an incident submission interface to display on a display of a user device, and receiving a set of partial inputs via the incident submission interface, wherein the set of partial inputs comprises a provisional incident description that is received as unstructured data;
(b) analyzing the provisional incident description to determine a quality score that indicates a level of descriptiveness and, in response to determining that the quality score is less than a maximal quality score, displaying one or more suggested changes via the incident submission interface, wherein the incident submission interface displays one or more user input controls to be selected by a user in response to the one or more suggested changes;
(c) in response to determining that the one or more suggested changes are displayed, receiving a user selection, via the one or more user controls, to cause the incident submission interface to revise the provisional incident description and receiving an incident dataset that includes an incident description as unstructured data via the incident submission interface, and pre-processing the incident description using a pre-processing function and based on a set of dictionaries, wherein each dictionary of the set of dictionaries defines a plurality of words and is associated with a dictionary type and a dictionary scope;
(d) using a core component function and based on the set of dictionaries, identifying a plurality of risk words in the incident description and mapping each of the plurality of risk words to one of a plurality of categorical risks to produce a set of core components;
(e) using a natural language processing ("NLP") function, comparing the set of core components to a set of prior incident data to identify one or more prior incident datasets that are similar to the incident dataset, wherein the set of prior incident data comprises a plurality of prior incident datasets that each describe a past incident; and
providing an incident alert to one or more user devices based on the one or more identified prior incident datasets.

18. The method of claim 17, further comprising, when pre-processing the incident description using the pre-processing function:
(a) identifying a language of the incident description, and where the language is not a supported language, translating the incident description to the supported language;
(b) removing punctuation from the incident description;
(c) removing a set of stop words from the incident description based on one or more stop word dictionaries of the set of dictionaries;
(d) removing a set of imprecise words from the incident description based on one or more imprecise word dictionaries of the set of dictionaries;
(e) creating a lowercase conversion description based on the incident description; and creating a tokenized description based on the incident description.

19. The method of claim 17, further comprising, when using the core component function:
(a) identifying the plurality of risk words in the incident description based on one or more risk word dictionaries of the set of dictionaries;
(b) for each risk word of the plurality of risk words, identifying a corresponding categorical risk of the plurality of categorical risks; and
(c) replacing each risk word in the incident description with the corresponding categorical risk for that risk word to produce the set of core components;
wherein a total number of risk words defined in the one or more risk word dictionaries is greater than a total number of the plurality of categorical risks.

20. A system comprising:
(a) an incident server comprising one or more processors;
(b) a set of dictionaries, wherein each dictionary of the set of dictionaries defines a plurality of words and is associated with a dictionary type and a dictionary scope; and
(c) a set of prior incident data, wherein the set of prior incident data comprises a plurality of
prior incident datasets that each describe a past incident;
wherein the one or more processors are configured to:
(i) cause an incident submission interface to display on a display of a user device, and receive a set of partial inputs via the incident submission interface, wherein the set of partial inputs comprises a provisional incident description that is received as unstructured data;
(ii) analyze the provisional incident description to determine a quality score that indicates a level of descriptiveness and, in response to determining that the quality score is less than a maximal quality score, display one or more suggested changes via the incident submission interface, wherein the incident submission interface displays one or more user input controls to be selected by a user in response to the one or more suggested changes;

(iii) in response to determining that the one or more suggested changes are displayed, receiving a user selection, via the one or more user controls, to cause the incident submission interface to revise the provisional incident description and receive an incident dataset that includes an incident description as unstructured data via the incident submission interface, and pre-process the incident description using a preprocessing function and based on the set of dictionaries;

(iv) using a core component function and based on the set of dictionaries:

(A) identify a plurality of risk words in the incident description based on one or more risk word dictionaries of the set of dictionaries;

(B) for each risk word of the plurality of risk words, identify a corresponding categorical risk of the plurality of categorical risks; and (C) replace each risk word in the incident description with the corresponding categorical risk for that risk word to produce a set of core components;

(v) using a natural language processing ("NLP") function, compare the set of core components to the set of prior incident data to identify one or more prior incident datasets that are similar to the incident dataset; and (vi) provide an incident alert to one or more user devices based on the one or more identified prior incident datasets;

wherein a total number of risk words defined in the one or more risk word dictionaries is greater than a total number of the plurality of categorical risks, and wherein the one or more processors includes at least one central processing unit ("CPU"), and does not include any graphical processing unit ("GPU").

* * * * *